United States Patent [19]

Pirie

[11] 4,351,840
[45] Sep. 28, 1982

[54] ANTIBACTERIAL ESTERS OF RESORCINOL WITH AMPICILLIN AND PENICILLANIC ACID 1,1-DIOXIDE DERIVATIVES

[75] Inventor: Donald K. Pirie, Uncasville, Conn.

[73] Assignee: Pfizer Inc., New York, N.Y.

[21] Appl. No.: 303,456

[22] Filed: Sep. 18, 1981

[51] Int. Cl.$^3$ .................... A61K 31/43; C07D 499/00; C07D 499/68

[52] U.S. Cl. ................................ 424/271; 260/239.1; 260/245.2 R

[58] Field of Search ..................... 424/271; 260/239.1, 260/245.2 R

[56] References Cited

U.S. PATENT DOCUMENTS 4,234,579 11/1980 Barth .................................. 424/246
4,244,951 1/1981 Bigham .............................. 424/250

FOREIGN PATENT DOCUMENTS 2061930 5/1981 United Kingdom .

Primary Examiner—Natalie Trousof
Assistant Examiner—Vera C. Clarke
Attorney, Agent, or Firm—Charles J. Knuth; Albert E. Frost; Robert K. Blackwood

[57] ABSTRACT

Bis-esters of resorcinol (1,3-dihydroxybenzene) with ampicillin or amoxicillin and penicillanic acid 1,1-dioxide or 6-beta-(hydroxymethyl)penicillanic acid 1,1-dioxide, having utility as antibacterial agents; processes therefor; and intermediates therefor, including m-hydroxyphenyl esters of penicillanic acid, 6-beta-(hydroxymethyl)penicillanic acid, and azidocillin.

21 Claims, No Drawings

ANTIBACTERIAL ESTERS OF RESORCINOL WITH AMPICILLIN AND PENICILLANIC ACID 1,1-DIOXIDE DERIVATIVES

BACKGROUND OF THE INVENTION

The present invention is concerned with bis-esters of resorcinol (1,3-dihydroxybenzene) with ampicillin or amoxicillin and penicillanic acid 1,1-dioxide or 6-beta-(hydroxymethyl)penicillanic acid 1,1-dioxide, their utility as antibacterial agents, particularly via the oral route of administration, and intermediates therefor.

Ampicillin and amoxicillin are well-known members of the penicillin class of antibiotics, widely used in clinical practice. The beta-lactamase inhibitors, penicillanic acid 1,1-dioxide and 6-beta-(hydroxymethyl)penicillanic acid 1,1-dioxide represent more recent discoveries (Barth, U.S. Pat. No. 4,234,579 and U.K. Patent Application No. 2,061,930, respectively). The latter compounds find utility in enhancing the effectiveness of such beta-lactam antibiotics as ampicillin and amoxicillin, in particular extending the spectrum to bacterial organisms otherwise resistant to ampicillin or amoxicillin because of their production of beta-lactamase.

Even more recently ampicillin, amoxicillin and other penicillins have been combined with beta-lactamase inhibitors such as penicillanic acid 1,1-dioxide in the form of 1,1-alkanediol esters (e.g. Bigham, U.S. Pat. No. 4,244,951).

SUMMARY OF THE INVENTION

The present invention encompasses antibacterial compounds of the formula

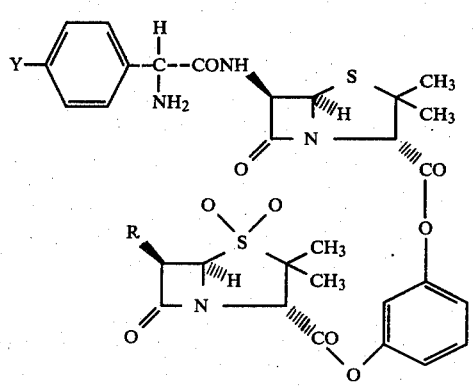

(I)

wherein Y is hydrogen or hydroxy and R is hydrogen or hydroxymethyl, together with the pharmaceutically acceptable acid addition salts thereof; the use of these compounds as antibacterial agents in mammals, particularly by the oral route of dosage; and intermediates of the formula

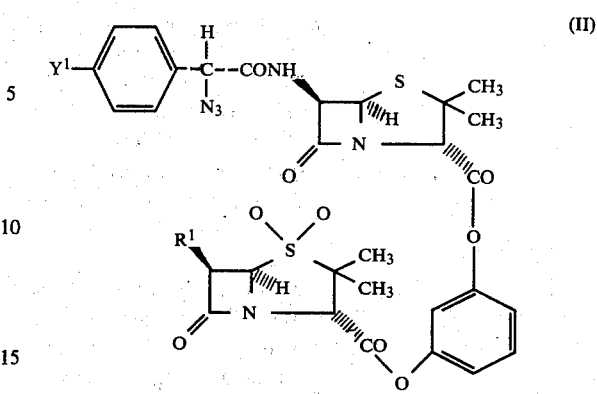

(II)

wherein $Y^1$ is hydrogen or benzyloxycarbonyloxy and $R^1$ is hydrogen or benzyloxycarbonyloxymethyl, as well as precursor half-esters of 1,3-dihydroxybenzene.

Pharmaceutically-acceptable acid addition salts of the compounds of the formula (I) include, but are not limited to those formed with hydrochloric, hydrobromic, nitric, phosphoric, sulfuric, fumaric, maleic, methanesulfonic, p-toluenesulfonic, citric and succinic acids. With polybasic acids, the salt can include more than one mole of base per mole of acid. However, the acid addition salts which are mole for mole are preferred.

The utility of the present compounds in the treatment of bacterial infections is reflected by the serum levels of ampicillin or amoxicillin and penicillanic acid 1,1-dioxide or 6-beta-hydroxymethylpenicillanic acid 1,1-dioxide achieved after parenteral, or more particularly, oral dosage in a test mammal. Treatment of bacterial infections with the penicillin and the beta-lactamase inhibitor, administered separately or as a physical mixture is already known as a highly effective antibacterial combination, in particular, against bacteria normally resistant or partially resistant to the penicillin through production of a penicillin destroying penicillinase enzyme.

DETAILED DESCRIPTION OF THE INVENTION

The final stage of the synthetic sequence employed for the preparation of the present antibacterial compounds of the formula (I) is accomplished by hydrogenation of the appropriate compound of the formula (II). The latter is dissolved or suspended in a reaction inert solvent medium in the presence of a catalytic amount of a noble metal catalyst and contacted with hydrogen at an appropriate temperature and pressure until reduction of the diazo group, and, if present, the benzyloxycarbonyl group(s), occurs. Thereafter the desired bis-ester of the formula (I) is isolated by conventional procedures involving recovery of the catalyst by filtration and recovery of product from the mother liquor by extraction, evaporation, chromatography, and crystallization as appropriate.

The expression "reaction inert solvent" refers to solvents which do not react with starting materials or products to significantly reduce the yield of the desired product. Polar organic solvents are generally suitable and include the lower alkanols such as methanol, ethanol, and isopropanol, etc., cyclic and straight chain water soluble ethers such as dioxane, tetrahydrofuran, diethylene glycol monomethylether, 2-ethoxyethanol, halogenated hydrocarbons such as methylene chloride, chloroform or ethylene dichloride, water, and mixtures thereof. As will be appreciated these solvents and others are conventional in known hydrogenation techniques applicable to the penicillin antibiotics and hence are not critical. The preferred solvents, however, are essentially anhydrous secondary alcohols, ethers and halogenated hydrocarbons, since side reactions involving destruction of beta-lactam ring are minimized in such media.

The temperature is no more critical in the present process than it is in other known hydrogenations of the penicillin antibiotics. Thus, the preferred temperature range is from about 0° to about 60° C., the more preferred temperature within this range being from about 10°–35° C. and most preferably room temperature.

The pressure employed during hydrogenation is not critical and is primarily dependent upon apparatus availability. In general, pressures of from atmospheric to 2,000 psi are satisfactory. Pressures below about 125 psi are preferred, since less complex equipment is required at such lower pressures.

The noble metal catalyst as employed in the present invention include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The catalysts may be preformed or formed in situ by prereduction of an appropriate salt of the catalytic compound. The preferred noble metal catalyst is palladium, preferably of the supported type. The preferred support is carbon.

The expression "catalytic amount" as used herein is well understood by those skilled in the art of known penicillin hydrogenation, i.e., it is the same amount as illustrated in the examples appearing herein.

The intermediate compounds of the formula (II) are prepared by acylation of a compound of the formula

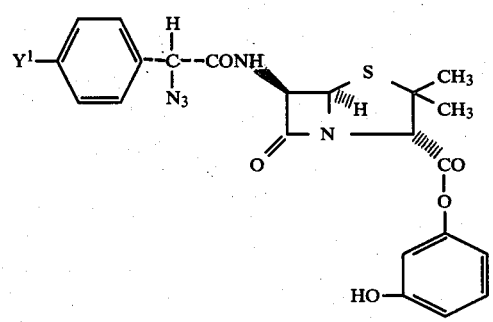

(III)

with an activated form of an acid of the formula

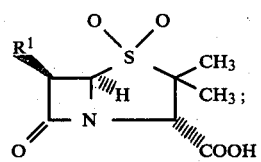

(IV)

or by acylation of a compound of the formula

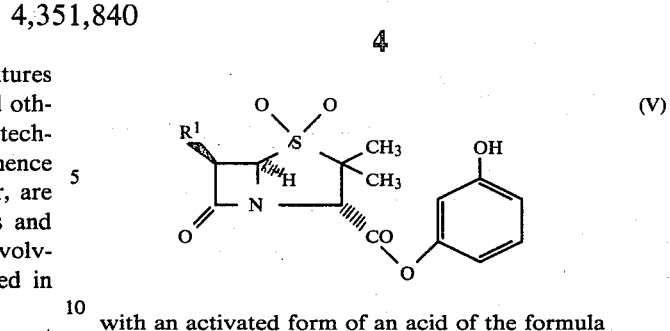

(V)

with an activated form of an acid of the formula

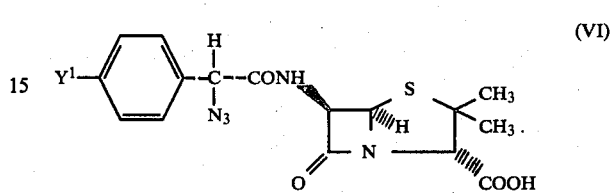

(VI)

In the formulae (III) to (VI), $Y^1$ and $R^1$ are as hereinbefore defined.

A convenient method for activating the acids (IV) and (VI) for the acylations of the preceding paragraph is to convert the acid to its acid chloride. For example, the corresponding sodium salt of the acid is reacted with an equimolar quantity of phosgene in a reaction inert solvent (as defined above), such as an ether (e.g. tetrahydrofuran), or a halogenated hydrocarbon (e.g. carbon tetrachloride, methylene chloride). A catalytic quantity of dimethylformamide or other N,N-dialkylcarboxamide is advantageously employed. The reaction is generally carried out below 25° C., as low as −25° C., but preferably in the range −5° to 10° C. The acid chloride is generally not isolated; rather the solution is reacted directly with the monoester of the formula (III) or (V), following the addition of at least one equivalent of a tertiary amine (e.g. pyridine). The acylation is carried out in the same solvent systems and in the same temperature range. The intermediate products of the formula (III) and (V) are isolated by conventional extraction and evaporation techniques.

Alternatively, the acid (IV) or (VI) is activated and condensed with the monoester (III) or (V) by use of a dehydrative coupling agent. The dehydrative coupling is accomplished by means of a wide variety of agents commonly used in peptide syntheses. Representative agents include N,N'-carbonyldiimidazole, N,N'-carbonyl-di-s-triazine, ethoxyacetylene, 1,1-dichlorodiethyl ether, diphenylketene p-tolylimine, N-hydroxyphthalimide, N-hydroxysuccinimide, N-hydroxypiperidine, ethylene chlorophosphite, diethyl ethylene pyrophosphite, N-ethyl-5-phenylisoxazolium-3'-sulfonate, phenylphosphorodi-(1-imidazolate) and carbodiimides such as dicyclohexylcarbodiimide, 1-cyclohexyl-3-(2-morpholinomethyl)carbodiimide, N-(3-dimethylaminopropyl)-N'-ethylcarbodiimide hydrochloride, 1-ethyl-3-(3'-dimethylaminopropyl)carbodiimide hydrochloride and diethyl cyanamide. The coupling agents are generally reacted first with the acid reactant and the resulting product then reacted without isolation with phenol-ester to afford the desired bis-ester.

The reaction is carried out in a reaction-inert solvent system in which the acid reactant need not be soluble. The only requirement for the solvent system is that it not enter into any appreciable reaction with the reactants or products. The variety of coupling agents which can be used to bring about the dehydrative coupling allow a wide choice of solvents. Representative solvents are N,N-dimethylformamide, tetrahydrofuran, dioxane, methylene chloride, nitromethane and acetonitrile.

The reaction of the acid reactant with the coupling agent is conducted at a temperature of from about 0° C. to about 60° C. The reactive intermediate is then reacted with phenol-ester of the formula (III) or (V) at from about 0° C. to 60° C. Each of these steps is advantageously carried out at from about 5° C. to about 25° C. since the yield of the reaction is improved.

The molar ratio of acid:coupling agent-phenol-ester (III or V) is generally about 1:1:1 to about 1:1.1:1.1. Higher ratios of coupling agent and phenol-ester can be used but offer no advantages. Excesses of ten mole percent are satisfactory.

As those skilled in the art will recognize, all reactants can be added at once rather than in stepwise fashion as described above. However, prior formation of the reactive intermediate (acid-coupling agent product) normally produces better yields of desired bis-ester (II).

Alternatively, the desired bis-esters of the formula (II) are synthesized by coupling the acids with the phenol-esters (III or V) using a mixed-anhydride procedure. In this case, the acids are first converted in situ to tertiary amine salt in the presence of a 1 to 1.1 molar excess of the amine. A variety of tertiary amines are suitable for this purpose. Exemplary are triethylamine, N-methylpiperidine, N-methylmorpholine, dimethylaniline or quinoline. Suitable reaction-inert solvents are methylene chloride, chloroform, dimethylformamide, and dimethylacetamide. It is preferable that the acid be completely dissolved by the excess of tertiary amine, usually requiring a stirring period, together with gentle warming, if necessary. The solution of amine salt is then reacted with an equivalent of alkyl (e.g. ethyl), benzyl, or phenyl chloroformate, at a temperature in the range of $-40°$ to 25° C., preferably in the range $-10°$ to 10° C., to form the mixed anhydride in situ. The mixed anhydride is reacted directly with the phenol-ester (III or V), preferably dissolved in a reaction-inert solvent which is of the same type as that used to prepare the mixed anhydride, to yield the desired bis-ester (II). The reaction is usually initiated at a cool temperature (such as $-40°$ to 15° C.), but allowed to warm to higher temperature (such as 5° to 20° C.) to complete the reaction. The typical molar ratio of acid:amine:chloroformate:-phenyl-ester (III or V) is 1:2:1:1 to 1:2.1:1.1:1.1.

The ester-phenols of the formulae (III) and (V) are analogously prepared by acylation of 1,3-dihydroxyphenol (resorcinol). Formation of the desired monoester is favored by using excess 1,3-dihydroxyphenol and by addition of the activated acid to the bis-phenol.

The starting materials required for the present syntheses are prepared according to literature methods, cited above, or as detailed in the specific examples below.

The pharmaceutically-acceptable acid addition salts of the antibacterial compounds of the present invention are readily prepared by standard methods. For example, an equivalent of the acid is combined with the free amine in an organic or an aqueous solvent. The salt is isolated by concentration and/or the addition of a nonsolvent. If desired, the salt can generally be isolated directly from a reaction mixture, without isolation of the free amine.

The utility of bis-ester compounds of the formula (I) is as exceptionally broad spectrum, systemic antibacterial agents. These compounds are useful clinically in the treatment of mammalian infections caused by any one of this broad spectrum of sensitive bacteria. The systemic utility of these compounds results from their in vivo hydrolysis to a mixture of the penicillin antibiotic (ampicillin or amoxicillin) and the beta-lactamase inhibitor (6-beta-penicillanic acid 1,1-dioxide or its 6-beta-hydroxymethyl analog).

The ultimate clinical utility of the bis-ester compounds against particular pathogenic bacteria is reflected by in vitro measurements of the activity of these penicillanic acid 1,1-dioxides against bacterially derived beta-lactamases, as well as by measuring the minimum inhibitory concentrations of a mixture of the penicillin with the beta-lactamse inhibitory compound. The detailed description and typical results of such studies follows.

The compounds of the present invention are thus evaluated in vitro by the ability of penicillanic acid 1,1-dioxide derivatives of the formula (IV) to inhibit the hydrolysis of beta-lactam antibiotics by beta-lactamase enzymes. The hydrolysis of ampicillin was determined by the microiodometric method of Novick [Biochem, J. 83, 236 (1962)]. Conditions for this assay are 0.5 M potassium phosphate, pH 6.5 and 37° C. Reactions were initiated by the addition of the cell-free beta-lactamase, except in the case of preincubation experiments in which the inhibitor and enzyme were incubated together in the assay mixture for 10 minutes before initiation of the reaction by addition of substrate. With the cellfree extracts of *Staphylococcus aureus, Escherichia coli, Klebsiella pneumoniae* and *Pseudomonas aeruginosa,* the substrate was ampicillin at 33 micro M (13 microg./ml). Typical specific activities of the beta-lactamase preparations were, respectively, 6,019, 88,970, 260 and 76 micromol/hr. per mg. of protein.

Cell-free extracts were prepared by sonic treatment (using three 30-s bursts at 4° C. except for *S. aureus,* which was broken with a French press) of cultures grown in brain heart infusion on a rotary shaker incubator. For the *S. aureus, P. aeruginose,* and *E. cloacae* strains, de novo synthesis of beta-lactamase was induced by growing a log-phase culture in the presence of a sublethal concentration of penicillin G at 100, 1,000, and 300 microg./ml, respectively, for 2.5 hr.

The beta-lactamase inhibiting activities of penicillanic acid 1,1-dioxide and its 6-beta-hydroxymethyl analog are summarized in Table I.

TABLE I

Activity of Compounds As Inhibitiors of Cell Free Beta-Lactamases

A. 6-beta-(Hydroxymethyl)penicillanic acid 1,1-dioxide (as calcium salt).
B. Penicillanic acid 1,1-dioxide (as sodium salt)

| Source of Beta-Lactamsase | Antibiotic (conc.) | A/B | Inhibitor (conc.) | | % Inhibition Beta-Lactam Hydrolysis |
|---|---|---|---|---|---|
| *Staphylococcus aureus* 01A400 | Ampicillin (33 μM) | A | 66 | μM | 98.3 |
| | | | 16.5 | | 78.8 |
| | | | 1.0 | | 39.3 |
| | | B | 66 | | 100 |
| | | | 16.5 | | 95 |
| | | | 1.0 | | 0 |
| *Escherichia coli* 51A129 | Ampicillin (33 μM) | A | 66 | | 100 |
| | | | 16.5 | | 100 |
| | | | 1.0 | | 95.7 |
| | | | 0.67 | | 92.1 |
| | | B | 66 | | 100 |

TABLE I-continued

Activity of Compounds As Inhibitiors of Cell Free Beta-Lactamases

A. 6-beta-(Hydroxymethyl)pencillanic acid 1,1-dioxide (as calcium salt).
B. Penicillanic acid 1,1-dioxide (as sodium salt)

| Source of Beta-Lactamsase | Antibiotic (conc.) | Inhibitor A/B | Inhibitor (conc.) | % Inhibition Beta-Lactam Hydrolysis |
|---|---|---|---|---|
|  |  |  | 16.5 | 100 |
|  |  |  | 1.0 | 97.0 |
| Klebsiella pneumoniae 53A129 | Ampicillin (33 μM) | A | 66 | 100 |
|  |  |  | 16.5 | 100 |
|  |  |  | 1.0 | 81.2 |
|  |  | B | 66 | 100 |
|  |  |  | 16.5 | 100 |
| Pseudomonas aeruginosa 52A104 | Ampicillin (33 μM) | B | 66 | 27.5 |
|  |  |  | 16.5 | 5.0 |

The in vitro activity of the compounds of the present invention is demonstrated by measuring the minimum inhibitory concentrations (MIC's) in mcg/ml of the beta-lactamase inhibitors together with the penicillin against a variety of microorganisms. The procedure which follows is the one recommended by the International Collaborative Study on Antibiotic Sensitivity Testing [Ericcson and Sherris, Acta. Pathologica et Microbiologia Scandinav, Supp. 217, Sections A and B: 64–68 (1971)], and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading tubes after 18 hrs. at 37° C. The susceptibility (MIC) of the test organism is accepted as the lowest concentration of compound capable of producing complete inhibition of growth as judged by the naked eye.

Results of experiments illustrating the enhancement of the effectiveness of ampicillin are shown in Table II. The manner in which the beta-lactam inhibitors (C and D) increase the effectiveness of ampicillin (E) can be appreciated by reference to experiments in which the MIC of ampicillin alone, and beta-lactam inhibitors (C) or (D) alone, are measured. These MIC's are then compared with the MIC values obtained with a combination of ampicillin and the beta-lactamase inhibitor. When the antibacterial potency of the combination is significantly greater than would have been predicted from the potencies of the individual compounds, this is considered to constitute enhancement of activity (synergy or pronounced synergy). The MIC values of combinations are measured using the method described by Barry and Sabath in "Manual of Clinical Microbiology", edited by Lenette, Spaulding and Truant, 2nd Edition, 1974, American Society for Microbiology.

TABLE II

MIC Values for 1:1 Mixtures of Ampicillin and beta-Lactamase Inhibitors

C. 6-beta-(Hydroxymethyl)penicillanic acid 1,1-Dioxide (sodium salt)
D. Penicillanic acid 1,1-dioxide (sodium salt)
E. Ampicillin

| Microorganism | MIC Values D | 1:1D:E | Response[a] D | MIC Values C | 1:1C:E | Response[a] C |
|---|---|---|---|---|---|---|
| Staphylococcus aureus 01A005 | 100 | ≦0.2 | NT | >200 | 0.39 | AT |
| Staphylococcus aureus 01A400 | 200 | 3.12 | PS | >200 | 3.12 | PS |
| Escherichia coli 51A266 | 25 | 3.12 | N | 50 | 3.12 | N |
| Citrobacter diversus 70C031 | 200 | 12.5 | PS | 200 | 25 | PS |
| Escherichia coli-R 51A129 | 200 | 100 | A | 50 | 12.5 | S |
| Pseudomonas aeruginosa 52A104 | >200 | >100 | NT | >200 | 100 | S |
| Klebsiella pneumoniae 53A079 | 50 | 12.5 | S | 50 | 6.25 | PS |
| Proteus morgani 57G001 | 200 | 12.5 | PS | >200 | 1.56 | PS |
| Serratia marcescens 63A095 | 200 | 6.25 | PS | 200 | 6.25 | PS |
| Enterobacter cloacae 67B009 | 100 | 25 | S | 100 | 12.5 | PS |

[a] PS = Pronounced Synergy
S = Synergy
A = Additive
N = Nothing
AT = Antagonism
NT = No Test The in vivo effectiveness of the bis-esters of the formula (I) is determined by measuring blood levels of the penicillin and of the beta-lactamase after dosage of the bis-ester to a mammal. Exemplary are the blood levels of ampicillin and penicillanic acid 1,1-dioxide in rats following oral administration of 20 mg./kg. of the bis-ester of the formula (I) wherein Y and R are each hydrogen. Blood samples were assayed at various time points using standard bioassay techniques. Ampicillin was assayed using Sarcina lutea as the microorganism, while penicillin was assayed using Pasturella 59B010 as the microorganisms. Results are summarized in Table III.

TABLE III

Serum Levels Following Oral Administration of m-(1,1-Dioxopenicillanoyloxy)phenyl Ampicillin Ester[a] to Rats (20 mg./kg.)

| Sample Time, min. | Average Serum Concentrations (microgm./ml.) | |
|---|---|---|
|  | Ampicillin | CP-45,899 |
| 15 | 1.08 ± 0.15 | 0.56 ± 0.006 |
| 30 | 1.07 ± 0.13 | 0.90 ± 0.08 |
| 60 | 0.43 ± 0.04 | 0.40 ± 0.03 |
| 90 | 0.29 ± 0.02 | 0.32 ± 0.08 |
| 120 | 0.21 ± 0.02 | 0.18 ± 0.05 |
| 180 | 0.08 ± 0.01 | 0.10 ± 0.04 |
| 240 | 0.08 ± 0.02 | 0.04 ± 0.03 |

TABLE III-continued

Serum Levels Following Oral Administration of m-(1,1-Dioxopenicillanoyloxy)phenyl Ampicillin Ester[a] to Rats (20 mg./kg.)

| Sample Time, min. | Average Serum Concentrations (microgm./ml.) | |
| --- | --- | --- |
| | Ampicillin | CP-45,899 |
| Area Under Serum Curve, μg./ml. hr. | 1.3 | 1.1 |
| T½, b-phase, hr. | 0.91 | 0.83 |

[a] Compound of the formula (I) wherein both Y and R are hydrogen.

When using an antibacterial compound of this invention in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the preferred oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g., polyethylene glycols having molecular weights of from 2000 to 4000. When aqueous suspensions are required for oral use, the active ingredient is combined with emulsifying and suspending agents. If desired, certain sweetening and/or flavoring agents can be added.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally and parenterally at dosages in the range from about 5 to about 100 mg. per kilogram of body weight per day, usually in divided doses. In some instances it is necessary to use doses outside these ranges.

The present invention is illustrated by the following examples. However, it should be understood that the invention is not limited to the specific details of these examples.

EXAMPLE 1 m-Hydroxyphenyl Penicillanate 1,1-Dioxide

Sodium penicillanate 1,1-dioxide (5.1 g., 0.02 mole) was stirred in 100 ml. of methylene chloride and 1 ml. of dimethylformamide at 0°–5°. Phosgene (1.98 g., 0.02 mole) in 18.8 ml. of carbon tetrachloride was added and the reaction mixture stirred at 0°–5° C. for 1 hour to form the acid chloride in situ. 1,3-Dihydroxybenzene (2.2 g., 0.02 mole) and pyridine (3.16 g., 0.04 mole) were then added and, after stirring at 0°–5° C. for 2 hours, the reaction mixture was washed with $3 \times H_2O$, dried ($Na_2SO_4$), filtered and evaporated to yield crude title product as a foam (4.5 g.). The crude product was chromatographed on silica gel, eluting with 1:1 hexane:ethyl acetate and monitoring by tlc. Clean product fractions [$R_f$ 0.42 (1:1 hexane:ethyl acetate)] were combined and purified title product isolated as a foam by evaporation [0.6 g.; ir ($CHCl_3$) 1780, 1808, 3586 $cm^{-1}$; $^1H$-nmr ($CDCl_3$) 1.55 (s, 3H), 1.7 (s, 3H), 3.4 (d, 2H), 4.63 (t, 1H), 4.6 (s, 1H), 6.6 (m, 3H), 7.25 ppm (m, 1H); m/e 325].

EXAMPLE 2 m-(1,1-Dioxopenicillanoyloxy)phenyl Azidocillin Ester

Sodium 2-azido-2-phenylacetamidopenicillanate (2.2 g., 5.54 mmoles) in 50 ml. of $CH_2Cl_2$ was stirred at 5° C. Phosgene (548 mg., 5.54 mmoles) in 5.65 ml. of $CCl_4$ was added and the mixture stirred at 0°–5° C. for 2 hours to yield the corresponding acid chloride in situ. Pyridine (583 mg., 7.38 mmoles) was added and then the title compound of the preceding Example (1.2 g., 3.69 mmoles). After stirring for 2 hours at 0°–5° C., the reaction was washed $3 \times H_2O$, dried ($Na_2SO_4$), filtered and evaporated to crude product. Chromatography on silica gel with 1:1 hexane:ethyl acetate as eluant and tlc monitoring [$R_f$ 0.22 (1:1 ethyl acetate:hexane)] gave purified title product [628 mg.; ir ($CHCl_3$) 2111; 1799–1789 $cm^{-1}$; $^1H$-NMR ($CDCl_3$) 1.55 (s, 3H), 1.7 (s, 6H), 1.75 (s, 3H), 3.47 (d, 2H), 4.61 (s, 1H), 4.64 (s, 1H), 4.68 (s, 1H), 5.1 (s, 1H), 5.31 (m, 2H), 7.23 ppm (m, 9H)].

EXAMPLE 3 m-(1,1-Dioxopenicillanoyloxy)phenyl Ampicillin Ester

Title product of the preceding Example (600 mg., 0.88 mmole) in 30 ml. of $CHCl_2$ and 30 ml. of isopropanol was hydrogenated over 600 mg. of 10% Pd/C at 25° C. and 50 psig for 75 minutes. The hydrogenation was monitored by tlc (19:1 $CH_2Cl_2$:$CH_3OH$; $R_f$ azide 1.0; $R_f$ amine 0.3). Upon completion, catalyst was recovered by filtration over diatomaceous earth, with $CH_2Cl_2$ wash. The combined filtrate and wash was evaporated to yield title product as white solids [0.5 g.; ir ($CHCl_3$) 1786–1805 $cm^{-1}$; $^1H$-NMR 1.55 (s, 3H), 1.6 (s, 3H), 1.69 (s, 6H), 3.47 (d, 2H), 4.6 (3s, 3H), 5.5 (d, 1H), 5.68 (m, 1H), 7.18 ppm (m, 9H)].

EXAMPLE 4 m-(1,1-Dioxopenicillanoyloxy)phenyl Ampicillin Ester Hydrochloride

Title product of the preceding Example (550 mg., 0.865 mmole) was stirred in $CH_2Cl_2$ (15 ml.), $H_2O$ (15 ml.) and isopropanol (5 ml.). The pH was adjusted to 2 with 4 N HCl. The organic layer was separated and combined with 15 ml. of fresh $H_2O$. The organic phase was removed by evaporation in vacuo. The resulting aqueous solution (still at pH 2.0) was combined with the original aqueous layer, extracted with ether, salted heavily with NaCl and extracted with methylene chloride. The methylene chloride extract was dried ($Na_2SO_4$), filtered and evaporated to yield title product as a white solid [380 mg.; $R_f$ 0.29 (19:1 $CH_2Cl_2$:$CH_3OH$)].

EXAMPLE 5 m-Hydroxyphenyl Azidocillin Ester

Sodium azidocillin (7.94 g., 0.02 mole) was converted to its acid chloride at 0°–5° C. as in Example 2. Pyridine (3.16 g.) and 1,3-dihydroxybenzene (2.2 g.) were added and the mixture stirred 2 hours at 0°–5° C. Crude product (8.4 g.) was isolated according to Example 2. Chromatography on silica gel, eluting with 2:1 CHCl$_3$:ethyl acetate and tlc monitoring, gave purified title product [0.23 g., R$_f$ 0.58 (2:1 CHCl$_3$:ethyl acetate); ir (CHCl$_3$) 1695 cm$^{-1}$, 1785 cm$^{-1}$, 1792 cm$^{-1}$, 3586 cm$^{-1}$, 2111 cm$^{-1}$; $^1$H-NMR (CDCl$_3$) 1.63 (s, 3H), 1.7 (s, 3H), 4.57 (s, 1H), 5.0 (s, 1H), 5.5 (m, 2H), 6.55 (m, 2H), 7.3 (m, 7H)]. Additional product is obtained by further chromatography of impure fractions.

EXAMPLE 6 m-(1,1-Dioxopenicillanoyloxy)phenyl Azidocillin Ester

Sodium penicillanate 1,1-dioxide is converted to its acid chloride according to Example 1, reacted with title product of the preceding Example, and present title product isolated and purified according to Example 3.

EXAMPLE 7

6-beta-Benzyloxycarbonyloxymethylpenicillanic Acid 1,1-Dioxide

A mixture of 6-beta-hydroxymethylpenicillanic acid 1,1-dioxide (2.29 g., 8.7 mmoles) and triethylamine (0.88 g.) in 40 ml. of CH$_2$Cl$_2$ is stirred at −10° C. Trimethyl chlorosilane (0.94 g.) is added and the ester allowed to form over 30 minutes at 0° to −10° C. A second equivalent of triethylamine (0.88 g.) is added, followed by carbobenzoxy chloride (1.48 g.). The mixture is stirred at 0° C. for 2 hours and then at room temperature for 30 minutes. Water (50 ml.) is added and the mixture shaken well to hydrolyze the trimethylsilyl ester. The pH is adjusted to constant pH 9 with aqueous Na$_2$CO$_3$. The aqueous phase is separated, adjusted to pH 1.5 with dilute HCl, extracted with fresh CH$_2$Cl$_2$, dried (Na$_2$SO$_4$), filtered and evaporated to yield title product as a foam.

EXAMPLE 8 m-Hydroxyphenyl 6-beta-Benzyloxycarbonyloxymethylpenicillanate 1,1-Dioxide

By the procedure of Example 1, the title compound of the preceding Example is converted to its acid chloride and reacted with 1,3-dihydroxybenzene to yield present title product.

EXAMPLE 9 m-(6-beta-Benzyloxycarbonyloxy-1,1-dioxopenicillanoyloxy)phenyl Azidocillin Ester By the procedure of Example 2, title compound of the preceding Example is converted to present title product.

EXAMPLE 10 m-(6-beta-Hydroxymethyl-1,1-dioxopenicillanoyloxy)phenyl Ampicillin Ester

By the procedure of Example 3, title compound of the preceding Example is hydrogenated to yield present title compound.

EXAMPLE 11

6-[2-(p-Benzyloxycarbonyloxyphenyl)-2-azidoacetamido]penicillanic Acid

The sodium salt of 6-[2-(p-hydroxyphenyl)-2-azidoacetamido]penicillanic acid (8.26 g., 0.02 mole) is stirred in 150 ml. of CH$_2$Cl$_2$ at 0° C. and reacted with trimethylsilyl chloride, then carbobenzoxy chloride according to the method of Example 7. Title product is isolated according to the same Example.

EXAMPLE 12 m-(6-beta-Benzyloxycarbonyloxymethyl-1,1-dioxopenicillanoyloxy)phenyl 6-[2-(p-Benzyloxycarbonyloxyphenyl)-2-azidoacetamido]penicillanate By the method of Example 2, title compound of the preceding Example is converted to its acid chloride and reacted with the title ester of Example 8 to yield present title product.

EXAMPLE 13 m-(6-beta-Hydroxymethyl-1,1-dioxopenicillanoyloxy)phenyl Amoxicillin Ester

By the method of Example 3, title compound of the preceding Example is hydrogenated to present title product.

EXAMPLE 14 m-(1,1-Dioxopenicillanoyloxy)phenyl 6-[2-(p-benzyloxycarbonyloxyphenyl)-2-azidoacetamido]penicillanate By the procedure of Example 2, title compound of Example 11 is converted to its acid chloride and then reacted with title ester of Example 1 to produce present title product.

EXAMPLE 15 m-(1,1-Dioxopenicillanoyloxy)phenyl Amoxicillin Ester

By the method of Example 3, product of the preceding Example is hydrogenated to yield present title product.

I claim:

1. A compound of the formula wherein Y is hydrogen or hydroxy and R is hydrogen or hydroxymethyl, or a pharmaceutically-acceptable acid addition salt thereof.

2. The compound of claim 1 wherein Y and R are each hydrogen.

3. The compound of claim 1 wherein Y is hydrogen and R is hydroxymethyl.

4. The compound of claim 1 wherein Y is hydroxy and R is hydrogen.

5. The compound of claim 1 wherein Y is hydroxy and R is hydroxymethyl.

6. A method of treating bacterial infections in a mammal which comprises treating said mammal with an antibacterially effective quantity of a compound of the formula

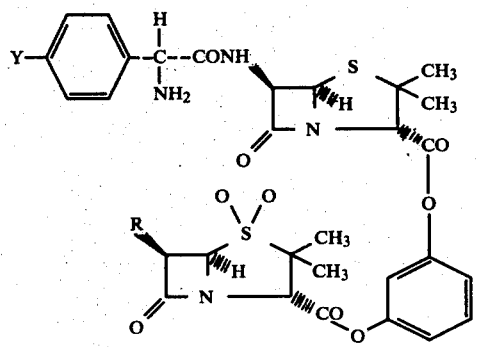

wherein Y is hydrogen or hydroxy and R is hydrogen or hydroxymethyl, or a pharmaceutically-acceptable acid addition salt thereof.

7. The method of claim 6 wherein Y and R are each hydrogen.

8. The method of claim 6 wherein Y is hydrogen and R is hydroxymethyl.

9. The method of claim 6 wherein Y is hydroxy and R is hydrogen.

10. The method of claim 6 wherein Y is hydroxy and R is hydroxymethyl.

11. A compound of the formula

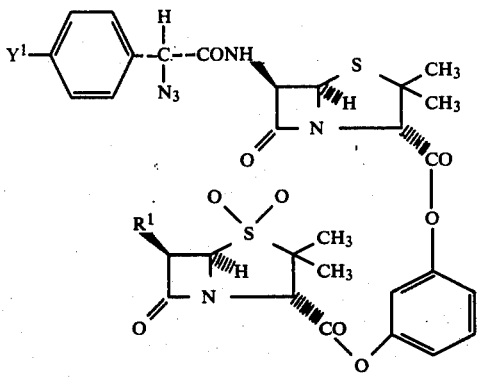

wherein $Y^1$ is hydrogen or benzyloxycarbonyloxy and $R^1$ is hydrogen or benzyloxycarbonyloxymethyl.

12. The compound of claim 11 wherein $Y^1$ and $R^1$ are each hydrogen.

13. The compound of claim 13 wherein $Y^1$ is benzyloxycarbonyloxy and $R^1$ is hydrogen.

14. The compound of claim 13 wherein $Y^1$ is hydrogen and $R^1$ is benzyloxycarbonyloxymethyl.

15. The compound of claim 13 wherein $Y^1$ is benzyloxycarbonyloxy and $R^1$ is benzyloxycarbonyloxymethyl.

16. A compound of the formula

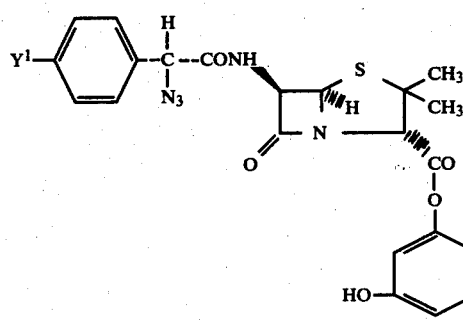

wherein $Y^1$ is hydrogen or benzyloxycarbonyloxy.

17. The compound of claim 16 wherein $Y^1$ is hydrogen.

18. The compound of claim 16 wherein $Y^1$ is benzyloxycarbonyloxy.

19. A compound of the formula

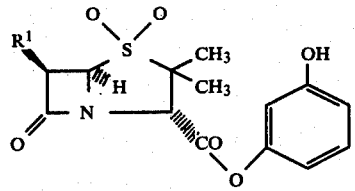

wherein $R^1$ is hydrogen or benzyloxycarbonyloxymethyl.

20. The compound of claim 19 wherein $R^1$ is hydrogen.

21. The compound of claim 19 wherein $R^1$ is benzyloxycarbonyloxymethyl.

* * * * *